United States Patent
Gokhfeld

[19]

[11] Patent Number: 6,073,480
[45] Date of Patent: *Jun. 13, 2000

[54] HUMIDITY SENSOR WITH DIFFERENTIAL THERMAL DETECTION AND METHOD OF SENSING

[75] Inventor: Yuzef Gokhfeld, Waltham, Mass.

[73] Assignee: Panametrics, Inc., Waltham, Mass.

[*] Notice: This patent is subject to a terminal disclaimer.

[21] Appl. No.: 09/005,766

[22] Filed: Jan. 12, 1998

Related U.S. Application Data

[63] Continuation-in-part of application No. 08/764,180, Dec. 13, 1996, Pat. No. 5,792,938.

[51] Int. Cl.$^7$ .................................................. G01N 19/10
[52] U.S. Cl. ........................................ 73/29.02; 73/335.05
[58] Field of Search ............................ 73/29.02, 335.02, 73/335.03, 335.05, 29.01; 374/28; 338/35

[56] References Cited

U.S. PATENT DOCUMENTS

| | | | |
|---|---|---|---|
| 3,523,244 | 8/1970 | Goodman et al. | 324/61 |
| 3,539,917 | 11/1970 | Chleck | 324/61 |

(List continued on next page.)

FOREIGN PATENT DOCUMENTS 2 047 431  11/1980  United Kingdom .

*Primary Examiner*—Hezron Williams
*Assistant Examiner*—Jay L. Politzer
*Attorney, Agent, or Firm*—Michael I. Falkoff; Nutter, McClennen & Fish, LLP

[57] ABSTRACT

A method of moisture measurement wherein a moisture responsive element is subjected to the measuring environment and its thermal capacitance or resistance temperature coefficient is measured. A system operates by cycling a sensor element between a first temperature and a second temperature and determining the sensor capacitance at each temperature. The sensor capacitance difference, corresponding to its temperature coefficient, is then compared to a previously compiled table of gas humidity or dew point versus capacitance increment values. The differential measurement thus made automatically corrects for systemic error originating in equipment drift, cable capacitance change and various aging and slow hysteresis or sensor capacitance variations. In one embodiment, a capacitive type relative humidity sensor is placed in thermal contact with an electric heater, a thermoelectric cooler, or both, and the heater and/or cooler are operated to drive the sensing element from a first temperature to a second temperature, under control of a microprocessor. Depending on the ambient temperature, the device may return to its initial temperature passively, or be actively driven by the heater or cooler, respectively. The frequency or cycle time of these temperature changes is selected to correspond to the time constant of the sensor, which in turn, may be a function of the relative humidity. In illustrative embodiments, a platinum film may be employed as the heater and a Peltier device may be employed as the cooler, and these are driven to change the sensor temperature and effect readings at upper and lower temperatures with time constant or cycle time of approximately 1–3 minutes. Preferably, a fixed cycle time is employed, and capacitance is measured at the upper and lower temperatures of each cycle with the sensor immersed in the sample environment, until the capacitance difference measurement stabilizes. This difference is then compared to a previously compiled table of differences for various dew points. In another embodiment or mode of operation, the thermal source is operated in two cycles or at two different power levels to drive the sensor to a first temperature $T_1$ away from ambient temperature, and to a second more divergent, temperature $T_2$. The temperature then returns to $T_1$ by passive interaction with the surroundings. By identifying the dew point curve by reference to capacitance difference between two fixed temperatures, errors and uncertainty at the high humidity/high temperature range are also reduced. In another embodiment, an occasional differential measurement is performed to detect errors in a set of stored curves and update the tables used for single-point humidity measurements, thus obviating the need for protocols involving reference gases or recalibration.

11 Claims, 6 Drawing Sheets

U.S. PATENT DOCUMENTS

| | | | |
|---|---|---|---|
| 4,143,177 | 3/1979 | Kovac et al. | 427/79 |
| 4,203,087 | 5/1980 | Kovac et al. | 338/35 |
| 4,277,742 | 7/1981 | Kovac et al. | 324/61 |
| 4,399,684 | 8/1983 | Advani et al. | 73/1 G |
| 4,419,021 | 12/1983 | Terada et al. | 374/101 |
| 4,568,875 | 2/1986 | Piso et al. | 324/61 |
| 4,677,416 | 6/1987 | Nishimoto et al. | 338/35 |
| 4,751,654 | 6/1988 | Lyyra | 364/482 |
| 4,877,329 | 10/1989 | Sauerbaum | 374/28 |
| 5,027,077 | 6/1991 | Yanagisawa et al. | 324/712 |
| 5,033,284 | 7/1991 | Belt et al. | 73/1 G |
| 5,156,045 | 10/1992 | Ponkala | 73/170 |
| 5,235,267 | 8/1993 | Schoneberg et al. | 324/71 |
| 5,274,334 | 12/1993 | Mills | 324/678 |
| 5,364,185 | 11/1994 | VanZandt et al. | 374/28 |
| 5,485,747 | 1/1996 | Antikainen et al. | 73/335.03 |
| 5,511,418 | 4/1996 | Antikainen et al. | 73/335.03 |
| 5,614,671 | 3/1997 | Morrissey | 73/335.03 |
| 5,644,080 | 7/1997 | Stormbom et al. | 73/335.05 |

PRESSURE OF AQUEOUS VAPOR

VAPOR PRESSURE OF ICE

PRESSURE OF AQUEOUS VAPOR OVER ICE
IN mm OF Hg

| TEMP. °C | 0.0 | 0.2 | 0.4 | 0.6 | 0.8 |
|---|---|---|---|---|---|
| 0 | 4.579 | 4.647 | 4.715 | 4.785 | 4.855 |
| 1 | 4.926 | 4.998 | 5.070 | 5.144 | 5.219 |
| 2 | 5.294 | 5.370 | 5.447 | 5.525 | 5.605 |
| 3 | 5.685 | 5.766 | 5.848 | 5.931 | 6.015 |
| 4 | 6.101 | 6.187 | 6.274 | 6.363 | 6.453 |
| 5 | 6.543 | 6.635 | 6.728 | 6.822 | 6.917 |
| 6 | 7.013 | 7.111 | 7.209 | 7.309 | 7.411 |
| 7 | 7.513 | 7.617 | 7.722 | 7.828 | 7.936 |
| 8 | 8.045 | 8.155 | 8.267 | 8.380 | 8.494 |
| 9 | 8.609 | 8.727 | 8.845 | 8.965 | 9.086 |
| 10 | 9.209 | 9.333 | 9.458 | 9.585 | 9.714 |
| 11 | 9.844 | 9.976 | 10.109 | 10.241 | 10.380 |
| 12 | 10.518 | 10.658 | 10.799 | 10.941 | 11.085 |
| 13 | 11.231 | 11.379 | 11.528 | 11.680 | 11.833 |
| 14 | 11.987 | 12.144 | 12.302 | 12.462 | 12.624 |
| 15 | 12.788 | 12.953 | 13.121 | 13.290 | 13.461 |
| 16 | 13.634 | 13.809 | 13.987 | 14.166 | 14.347 |
| 17 | 14.530 | 14.715 | 14.903 | 15.092 | 15.284 |
| 18 | 15.477 | 15.673 | 15.871 | 16.071 | 16.272 |
| 19 | 16.477 | 16.685 | 16.894 | 17.105 | 17.319 |

USE TEMPERATURES LISTED AS:

DEW POINTS
FROST POINTS
AMBIENT OR ACTUAL GAS TEMPS.

USE VALUES LISTED FOR:

P (PARTIAL PRESSURE $H_2O$)
$P_S$ (SATURATED VAPOR PRESSURES)

*FIG. 2*

HUMIDITY SENSOR WITH DIFFERENTIAL THERMAL DETECTION AND METHOD OF SENSING

REFERENCE TO RELATED APPLICATIONS

This application is a continuation-in-part of Ser. No. 08/764,180, filed on Dec. 13, 1996, now U.S. Pat. No. 5,792,938, and also includes material from International Application PCT/US97/22862 filed Dec. 12, 1997, the priority of which is duly claimed under 35U.S.C. §120.

BACKGROUND

This invention relates in general to the measurement of moisture, i.e., water vapor or dew point in a gas, and more particularly to such measurement using a compact solid state sensor which provides rapid measurement of absolute humidity or dew point over a wide range of temperature and pressure conditions.

The technique for performing a measurement of this sort has evolved, from the nineteenth century approach of plotting the temperature differential between dry and wet bulb thermometers, to modem systems wherein a small well-defined circuit element or structure which changes its resistance or capacitance in response to the surrounding humidity, is adapted to sense humidity in diverse process or measurement environments. By making the active circuit element thin or small, one is able to provide an instrument which reaches equilibrium with the atmosphere relatively quickly, and by utilizing films of material such as polymer or ceramic, these instruments may be relatively long-lived, such-that the compilation of a table of operating parameters is readily carried out and can remain in effect or be recalibrated to achieve accuracy, or at least repeatability, for extended periods of time.

One example of this approach to humidity sensing instrumentation is shown in U.S. Pat. No. 3,523,244. That patent shows a sensor element in which an aluminum oxide layer approximately one quarter of a micron thick is formed on a conductive substrate and covered with a thin conductive but porous top surface electrode. The oxide layer, a hard hydrated form of aluminum oxide with an irregular pore structure, allows water vapor to permeate or diffuse through its thickness. This material takes on water in proportion to its partial pressure in the surrounding atmosphere, and changes in both its resistance and its capacitance are readily measured between the substrate and the surface electrode. As noted above, because of the relatively small thickness of the active layer, the element responds quickly to the surrounding humidity, with a response time normally ranging from a fraction of second to several minutes, depending on degree of saturation, and has a wide range for humidity levels that change over a range of several orders of magnitude.

Readout of such a device is accomplished with conventional circuitry of the type used for a great number of capacitive or resistive sensors, such as load cells, diaphragm-type capacitive differential pressure measuring instruments, and others. This may be done with a capacitance measuring bridge, or other such circuit. For example, a square or sawtooth wave oscillation of a few hundred to a few thousand Hz may be provided across the element to cyclically charge and discharge the sensor, and the voltage developed on the sensor may be synchronously sampled, amplified, rectified, and output as a normalized (e.g., zero to one volt) signal. In various embodiments, the direct voltage readout may be strictly proportional to absolute humidity or otherwise reflect the humidity reading in a particularly simple fashion. More generally, the capacitance will vary both with humidity and with temperature of the element, and readout is accomplished by having first compiled a table of the output values, and stored the table, and then applying the correct calibration scale from the stored table for the given temperature, pressure or other directly measured condition.

In addition to hydrated ceramic films as described in the above-referenced '244 patent, a number of films of a polymer, such as a polysulphone or other material, have been used as the water-sensitive layer to enhance the response, stability or other characteristics of the sensor.

One method for using such sensors is to first obtain a sensor calibration curve of the sensor capacitance for each relative humidity at fixed temperature. The calibration curves are stored. Then, when a sensor is used in the field, a sample gas with an unknown relative humidity or dew point is applied to the sensor. The corresponding capacitance value is measured, the unknown relative humidity can be found by finding the corresponding value on the previously compiled capacitance versus relative humidity calibration curve. When the relative humidity and sensor temperature are both known, the corresponding dew point is also uniquely determined and may be found or interpolated empirically from widely available tables of saturated water vapor pressure versus temperature. However, since the sensor is in general quite small, the above methodology implicitly measures the sensor capacitance or resistance at the temperature of the test gas, and this requires that the calibration curve be obtained and stored for all temperature levels at which the element is to be used. Other measures of moisture content may be used for the initial calibration or the subsequent measurements.

While in theory this measurement can be made quite accurate, in practice, a number of possible sources of error are inherent in the methodology. First, any temperature detection error leads to reliance on an inappropriate calibration curve. Second, as a practical matter calibration curves are compiled at the time the sensor is built or installed, so that sensor "aging" over time may cause its characteristics to depart from those originally measured. Third, some hysteresis error may arise because the process of detection relies on the absorption or desorption of water from the thin layer, and the driving forces for the mechanics of equilibration may be affected by the previous level of humidity measured, so that the current measurement reading will depend on the previous relative humidity and the time interval during which the new and different level has been applied to the sensor. This memory effect may last for days or weeks. Furthermore, systematic errors of the measuring instrument such as errors in capacitance measuring bridges, in volt meters, parasitic capacitance of connecting cables, or changes in capacitance due to bending or realignment of wires, or changes in other circuit parameters that occur with temperature, may all contribute to inaccuracies of the fundamental signals or of their conversion to humidity measurements.

A number of these sources of error can be overcome in a sophisticated measurement environment by processes of recalibrating or reinstalling the equipment, protocols for baking out or zeroing the sensor, and by initializing or purging processes such as applying a reference dry gas for a known period of time, or other processes which may be specific to the sensor or electronics under consideration. Furthermore when operated with a microprocessor-controlled circuit, as is commonly done, tables of normal aging characteristics may be built into the device, allowing an estimated correction factor to be applied for some of these effects. However, a standard correction protocol, even one involving a constant offset plus a linear term, can only be expected to achieve accuracy in the middle range of moisture parameter values, e.g., 1–95% RH. For the measurement of trace moisture levels, where equlibrium is achieved slowly and the effects of drift and slow processes occur, little or no improvement may be obtained by simple or formulaic updating of the original calibration table.

Theoretically, this may be understood as follows. The commonly used or conventional capacitance versus moisture calibration curve can be represented by the formula $$C = C_o + F(\text{moisture}) \quad (1)$$

Classical sensor sensitivity is $\Delta F/\Delta(\text{moisture})$, with a typical value of about 0.4 pF/% RH, while the moisture content of the gas may be expressed in any appropriate units of choice (partial pressure, RH, Dew/Frost Point, etc.). Both $C_o$ and F(moisture) can be found by the experimental procedure commonly followed for initial sensor calibration, i.e., by placing the sensor in a series of known humidity gas environments and measuring the characteristics, tabulating and storing the results. Subsequently, by measuring sensor capacitance C, one can find $$F(\text{moisture}) = C - C_o \quad (1')$$

and thus, the moisture content itself.

However, it is well known that $C_o$ and F(moisture) retain their initial values only for relatively short period of time after calibration. Because of variety of reasons such as sensor "aging", failure to fulfill equilibrium conditions, "memory" effects from the preceding environment, stray capacitance changes, and the like, $C_0$ and F(moisture) gradually deviate from their initial values. Thus, after some time "true" calibration curve or actual current response will have the form $$C = (C_o + \delta C_o) + F(\text{moisture}) * \alpha$$

where $\delta C_o$ is a function of time, which is commonly known as the zero drift.

The coefficient a represents the calibration curve "slope" and can be reasonably assumed equal 1 for a relatively long period of time, e.g. several months or longer. This assumption is based on experimental data, at least in a clean background gas environment, and as a practical matter does not introduce additional error in the typical low-end measurement range, below 5% RH.

At the time of measurement, the moisture content can then be found by the formula $$F(\text{moisture}) = C - (C_o + \delta C_o) \quad (2)$$

Unfortunately, $\delta C_o$ is not generally known, unless the sensor has been recently re-calibrated. The common solution is to substitute for $(C_o + \delta C_o)$ in equation (2), at the time a measurement is made, simply the original $C_o$ found at the time of initial calibration. This will give an uncertainty of $\pm \delta C_o$ in the resulting F(moisture) value, and results in a moisture measurement error typically from 0.5% to 2% RH.

It is possible to improve measurement accuracy by using an in situ recalibration using an analytical model and an abbreviated set of measurements, such as several capacitance measurements at different temperatures with at least one "absolute" measurement of 100% RH obtained by cooling the sensor to the dew point or frost point. These data points are then used to update the current values of $C_o$ as well as sensor sensitivity, and thus update the stored calibration curve. One such approach is shown in U.S. Pat. No. 5,033,284, which reports a method using a heated or cooled sensor for obtaining the required data points. As a practical matter, corrections of this sort are adequate when the sensor is used in a mid-range of RH measurement values from few % to 100% RH. It relies on the fact that temperature change at constant water partial pressure can be used to simulate water pressure change at constant temperature.

Several limitations, however, do not allow this method to be extended to very low moisture ranges, for example to measurements of gas Frost point below about −40° C. and RH below about 0.5%. In addition to the above-mentioned requirement that one of the temperature data points be as low as the Frost Point, the analytic models used for calculation to update the calibration curves do not take into account the particular properties of the individual sensor. For instance, the calibration curve's coefficients $C_o$ and $\alpha$ are implicitly assumed to be independent of temperature. However, in practice, the coefficient $C_o$ exhibits a temperature drift equivalent to at least 0.01% RH per ° C., and a more typical average value of this quantity is 0.05% to 0.2% per ° C. for temperatures T<23° C. Since the new data points themselves require a temperature change of many tens of degrees Celsius, this factor alone yields a calibration curve error at least ~0.5% RH. In addition, any series used to represent a real calibration curve should be limited to a few first terms, and for accuracy, it is necessary to establish sensor-moisture equilibrium at each temperature point during calibration and when taking moisture measurements as well. These conditions severely limit the range and utility of such corrections.

Overall it may be said that the development of solid state humidity sensors and associated instrumentation have led to relatively hardy and compact embodiments of sensors capable of making repeated measurements, but these measurements, because of the underlying physics of the sensor and electrical signal processing, possess limitations that should be addressed.

It would therefore be desirable to provide a humidity sensor of enhanced accuracy, stability or ease of calibration.

SUMMARY OF THE INVENTION

The method of this invention is based on the general observation that moisture sensors such as capacitance-type polymer sensors of the type commonly used as Relative Humidity (RH) sensors, exhibit a change in capacitance when the sensor temperature changes, even if the partial pressure of water vapors remains the same. That is, their characteristics may be graphed as a two-dimensional surface defined over the variables temperature and moisture. While conventional measurement systems store a family of one-dimensional slices of this characteristic function as their look-up references, the nature of those curves is subject to aging and discrete offsets, and is inherently inaccurate at extremes of humidity, such as at very low humidity values where noise and offsets can entirely mask the signal. Furthermore, the response time required for an effective measurement at even moderately low humidity increases greatly. Applicant's invention looks to the form of the two-dimensional moisture/temperature response to provide reference points which are more stable and cover a greatly extended range. Briefly applicant calibrates a sensor by measuring its thermal coefficient between two temperatures, and then performs measurements by driving the sensor between temperatures and taking a differential measurement in the sample environment. The response time remains quite fast, even at extremely low moisture values where moisture equilibration of the sensing film is a slower process. The differential measurement allows the same sensor chip to be used with higher accuracy over an extended range and greater lifetime, to be used occasionally to recalibrate existing sensors used in conventional single point measurement systems, and to provide a direct measure of absolute humidity.

The present invention exploits the temperature dependence of the RH sensor output, using a different sensor output parameter from that conventionally used, and correspondingly, an entirely different calibration curve, to eliminate the poorly behaved $C_o$ from the measurement. The key idea is to use the sensor capacitance increment or variation induced by sensor temperature change as the sensor output or fundamental measurement parameter. Correspondingly, the stored calibration values $\Delta C$ for the expected range of moisture values are used to convert this parameter to a moisture reading. The sensor is preferably operated between two fixed temperatures, and the system may require a measurement of ambient temperature when a relative, rather than absolute moisture measurement, such as relative humidity (RH) is desired.

This is achieved in accordance with a method of humidity measurement of the present invention wherein a humidity responsive element is subjected to the measuring environment and its thermal capacitance or resistance coefficient is measured. A representative device operates by cycling the sensor element between a first temperature and a second temperature and determining the sensor capacitance at each temperature. The sensor capacitance difference, or thermal coefficient of capacitance, is then taken as the measurement quantity, and is looked up in a previously compiled table of gas dew point versus capacitance increment calibration curves. The differential measurement thus made is free from systematic error originating in equipment drift, cable capacitance change and various aging and slow hysteresis or sensor capacitance variations. Furthermore, initial calibration requires only a set of $\Delta C$ vs moisture curves rather than a full matrix of calibration points, since the sensor temperature, rather than the ambient temperature, determines the sensor reading.

In one embodiment, a capacitive type relative humidity sensor is placed in thermal contact with an electric heater, a thermoelectric cooler, or both, and the heater and/or cooler are operated to drive the sensing element from a first temperature to a second temperature which is preferably done under control of a digital device such as a microprocessor control chip, or under control of simple analog devices such as thermal cut-off or cut-in switches. Depending on the ambient temperature, the device may return to its initial temperature passively, or be actively driven by the heater or cooler. The frequency or cycle time of these temperature changes is selected to correspond to the time constant of the sensor in the ranges of temperature and relative humidity of the intended sample gas, and measurement is preferably made at each temperature end point. In illustrative embodiments, a platinum film may be deposited in or on the substrate below the sensing film and energized at a controlled power level to heat the film. A Peltier device may be employed as the cooler. These are driven to change the sensor temperature between two fixed temperatures, with a time constant or cycle time of several seconds or several minutes, and upper and lower readings are made at the two temperatures to determine the differential reading which is looked up in a table of calibration values previously compiled with reference gases at the same two temperatures. Preferably, a fixed cycle time is employed, and capacitance is measured at the lower and upper temperatures successively in each cycle with the sensor immersed in the sample environment. The measured capacitance difference is then compared to the previously compiled table of $\Delta C$ vs. dew point for the range of dew point values.

Alternatively, such differential measurement may be taken only at a greater interval or more prolonged time period—for example, weeks or months—during which time conventional C vs Moisture calibration table look-up measurements are performed. In that case, the more accurate $\Delta C$ measurement so obtained is then used to determine the actual moisture value. If the currently measured capacitance yields a different value from that given by the $\Delta C$ measurement, then the conventional stored capacitance calibration tables are corrected or updated to matched the changed response of the sensor. A $\Delta C$ measurement sensor may thus be used to recompile the calibration table of a separate, conventional, sensor, thus avoiding the time-consuming and expensive process of recalibration hitherto-fore necessary for aging sensors. The updated C vs. dew point table so obtained is then used alone for a time, applying a standard conversion procedure to determine dew point measurement results. For this recalibration protocol, both measurements (i.e., the conventional one based on C measurement, and $\Delta C$ differential measurement in accordance with this invention) are assumed to be made practically at the same time and with the same gas portion, so the humidity data obtained from each single $\Delta C$ differential measurement is sufficient to provide one point calibration of the conventional C vs. dew point calibration curve. In other words, the same current value of sample gas humidity is simultaneously measured by two different methods, a $\Delta C$ differential measurement method to determine the correct calibration curve, followed by a one point C measurement and look up, in the conventional manner, on a stored humidity curve. The conventional method is then used for some time alone e.g. over a period of hours, days or longer, after which another $\Delta C$ difference measurement result is obtained and used for another calibration as described above.

The $\Delta C$ differential measurement is readily performed in a very short time, e.g., within a 5 to 15 second time interval, so by providing an automated controller to effect the $\Delta C$ measurement and re-calibration, the correction process is "transparent", i.e., not noticeable and does not delay the conventional method of humidity measurement. In this embodiment, the time period between calibrations may be set depending on the time period during which the conventional measurement remains stable, e.g., one hour, day or week, which may be a function of the process or measurement environment.

The invention also contemplates that a more sophisticated algorithm be embodied into a microprocessor based controller. By way of example, the $\Delta C$ difference measurement protocol can be temporarily suspended and a convetional single point reading taken as long as change in the consecutive conventional measurements remains greater than a preset threshold, indicating an unsteady environment. The controller then performs a recalibration or reverts to $\Delta C$ measurements when the threshhold is not exceeded. This minimizes $\Delta C$ differential measurement dynamic error.

In one embodiment of a device for carrying out the method, a heater is provided to heat the sensor and the sensor is operated in two cycles or at two different heater power levels to drive the sensor to a first temperature $T_1$ above ambient temperature, and to a second higher, temperature $T_2$. The temperature then returns to $T_1$ by passive cooling, and may again be driven to $T_2$. At each temperature a sensor reading is taken, and the difference between readings forms the sensor output. In another embodiment a Peltier cooler is placed in thermal contact with the sensor, and it is operated to decrease the temperature of the sensor element to one or more levels $T_{-1}$, $T_{-2}$ below ambient. Again, the sensor may return to the higher temperature by passive interaction with the surroundings. In yet a third embodiment the system includes both a heater and a cooler, and the sensor element is actively driven to the two temperatures at which its capacitance is measured. By actively driving the device to $T_1$, then to $T_2$, then back to $T_1$ in a known cycle time, the memory effects are made repeatable, and are a function of the cycling conditions. These may be accurately represented in the ΔC-dew point calibration table, which is compiled at the same temperatures with the same cycle interval. Applicant has found this measurement technique to be extraordinarily accurate and stable over time when subsequently, measurements are made by employing the same thermal cycle time and endpoint temperatures as used in compiling the calibration table. The sensing system is particularly useful at low moisture levels, below 5% RH and at low temperatures.

BRIEF DESCRIPTION OF THE DRAWINGS

These and other features of the invention will be understood from the description below, taken together with the background art and the Figures herein representing illustrative embodiments and operation of the invention, wherein

FIG. 2 is a table showing humidity as a function of temperature and dew point;

DETAILED DESCRIPTION

Figure 1:
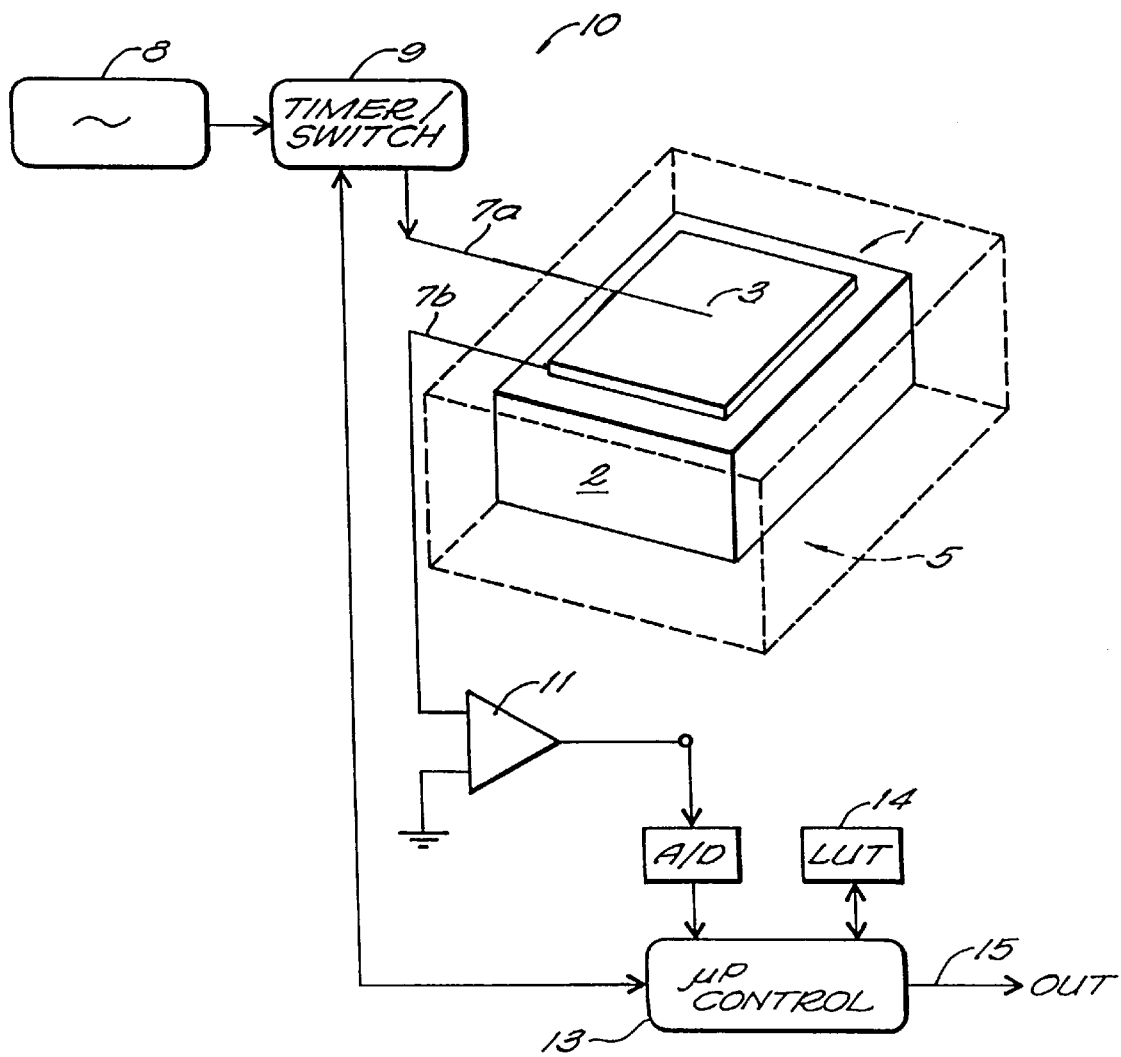
FIG. 1 illustrates a prior art humidity sensor.

FIG. 1 shows a general schematic drawing of a humidity sensing system, shown in a generality which is applicable to the present invention and to the prior art. As shown, the system 10 includes a sensing element 1 comprising at least a substrate 2 and an active humidity sensing layer 3, and an environmental chamber 5 illustrated in phantom in which the sensing element 1 resides. Electrodes 7a, 7b connect to opposing sides of the active layer 3 which, as illustrated is a thin film which responds to humidity in the environment. The sensing element 1 is placed in a measurement circuit which, simply by way of example, is illustrated as including an oscillating signal source 8, a timer and switching unit 9, such as a flip flop or microprocessor controlled switch or switch array, and an amplifier 11 which may be operated in various embodiments synchronously or with a partial duty cycle to produce an output signal representative of the capacitance or other electrical characteristic of the sensor 1. As shown in FIG. 1, this output is digitized and fed to a microprocessor or controller 13 which compares the output signal to signals stored in a look-up table 14 and determines the corresponding values of relative humidity, partial pressure or dew point to which the sensor is subjected. This humidity value is produced as an output signal on line 15 and may for example be fed to a panel display or be output to a printer, digital storage device or other form of recorder or display.

In general, the measured sensor property such as capacitance of the active layer 3 will be proportional to the dielectric constant ε of the material times its surface area divided by its thickness, and as noted above, the thickness is generally small, well under one mil to assure a fast response time. For alumina or typical polymer films, a dielectric constant ε is about 3 to 5, while that of water is 81, so that as water is gained or lost in the active layer, the capacitance of the element will increase or decrease respectively. In general, the level of moisture in the plastic film will be proportional to the pressure of moisture in the air and will also be a function of surrounding temperature. The final output may be calibrated either in absolute terms of grams of water per cubic meter, as a partial pressure of water vapor in the total gas, or as a dew point measurement; that is, as a temperature T at which the saturated water vapor pressure would be equal to the measured water vapor pressure. The moisture measurement may also be reported out in relative units, i.e. as a relative humidity.

FIG. 2 shows a representative portion of a table of aqueous vapor pressure over ice in millimeters of mercury for a temperature range of 0 to 20 degrees centigrade. These empirical tables are conventionally used for straightforward conversions between the various forms of humidity output measurement. However, as an initial step, the capacitance of the sensor must be compiled over the expected range of temperature and humidity operating conditions.

As applied to a sensor described above, a typical film capacitance may be around 200 pF at zero humidity, and would generally rise with increasing water vapor in the surrounding air. In general, the uptake or release of water may be physically modeled as an equilibrium process going on at the surface of the polymer sensing firm, between water molecules on the surface having a relatively low energy and water molecules in the surrounding vapor. In general, the energy of water molecules in the gas is higher, and the bound molecules are able to escape from the surface as the temperature rises and a greater proportion of the surface molecules acquire a higher energy.

The saturation pressure may be represented as $P_S = P_{S_o} e^{\Delta E_1/RT}$ where $\Delta E_1$ corresponds to the difference in energy of a free water molecule and a bound (liquid) molecule, and R is the Boltzmann constant. Because of this equilibrium process, while the saturation pressure of humidity in a gas will increase sharply with temperature, the capacitance of the sensor will decrease with temperature due to the shift in distribution between liquid and gaseous water, decreasing the amount of water residing in or on the sensing film. The horizontal asymptote makes it difficult to obtain accurate readings at high temperatures and saturation.

The general form of these curves is a nested family of curves, which are invertible, in the sense that a capacitance reading at a known temperature can be converted to a specific humidity or dew point value.

Figure 3:
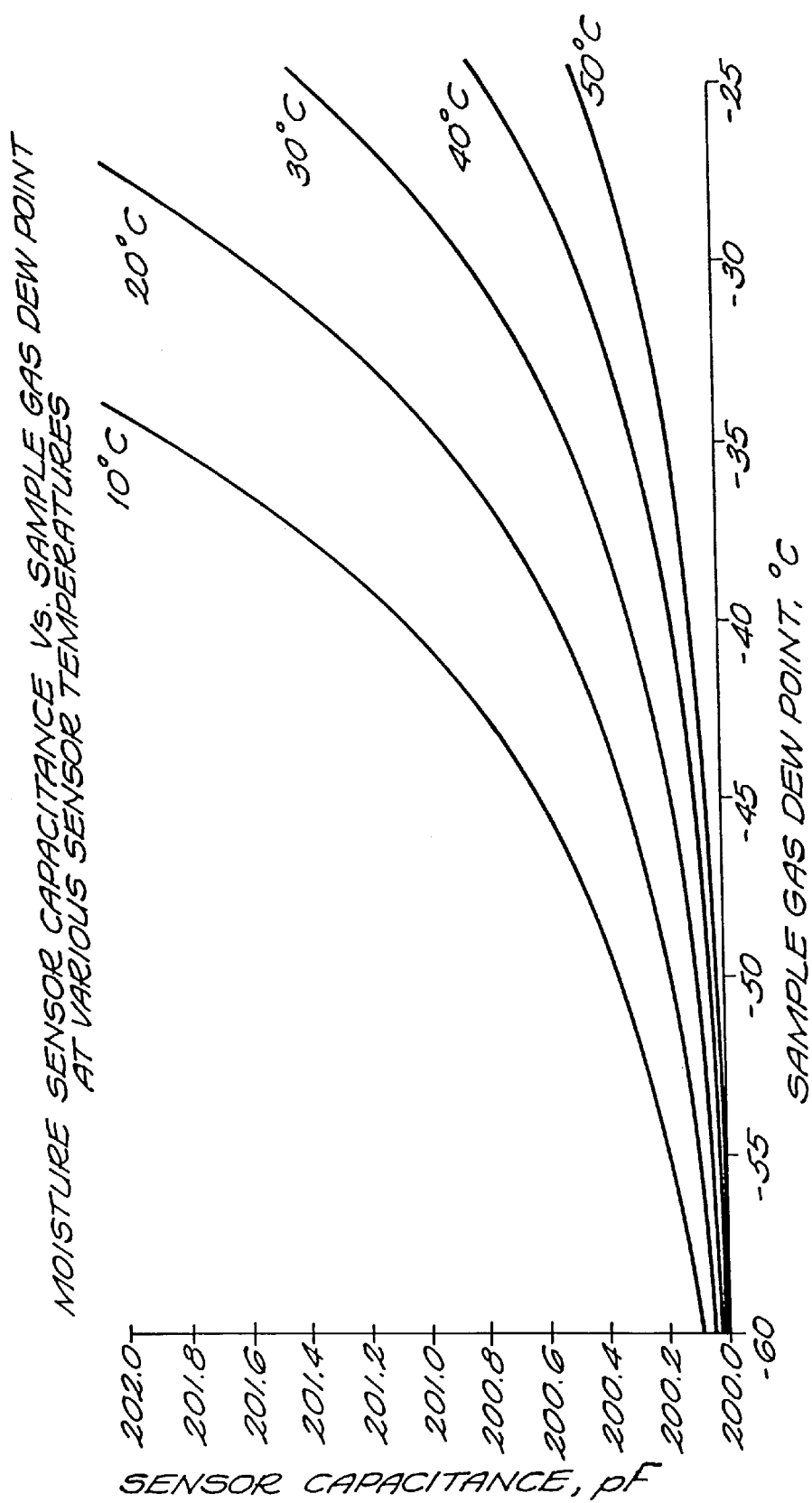
FIG. 3 is a graph showing sensor capacitance as a function of dew point at various temperatures.
Figure 3A:
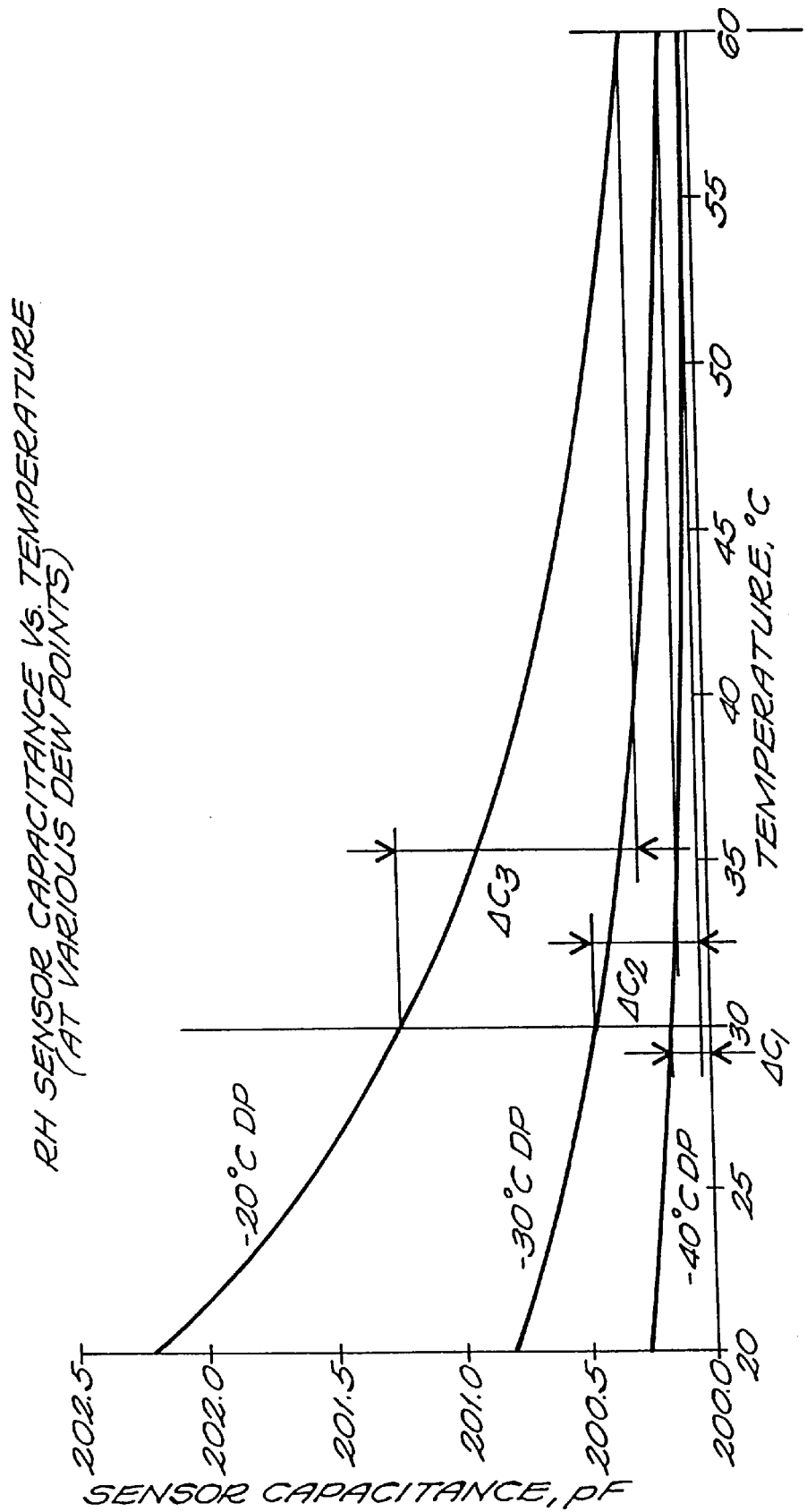
FIG. 3A is a graph showing sensor capacitance as a function of temperature at various dew points.

As noted above, the humidity sensor resistance and/or capacitance is a function of both humidity and temperature. This function is customarily represented as a family of capacitance vs. gas dew point curves for a set of different temperatures, as shown in FIG. 3, or capacitance vs. temperature curves for several different sample gas dew point values as shown in FIG. 3A. The gas temperature may be assumed to coincide with the sensor temperature at least on the sensor surface. For prior art devices, these characteristic capacitance curves are generally compiled at the time the system is manufactured or assembled, using a time-consuming calibration procedure with reference gases of known moisture content at various temperatures.

Empirical tables of aqueous vapor pressure over ice at different temperatures as shown in FIG. 2 or well known equivalents are conventionally used for straightforward conversions between the various units of humidity output measurement. Using such tables, the capacitance vs. dew point and temperature function as shown in FIG. 3 and FIG. 3A can be transformed into capacitance vs. pressure, relative humidity or any other unit of moisture measurement which is desired for the measurement application involved. An additional parameter may be measured for effecting some of these conversions, and this is readily provided by a separate sensor, such as a pressure sensor. For example a gas pressure reading is needed to transform dew point or partial pressure into units of grams of water per kilogram.

However, as an initial step, the capacitance of the sensor vs. humidity/temperature function must first be determined by the calibration protocol and stored for reference over the range of expected operating conditions, and must be represented in terms of at least one of the units of the moisture measurement.

FIG. 3 shows a typical such family of calibration curves for effecting prior art measurement, with sensor capacitance in picofarads plotted against sample gas dew point, for a range gas temperatures between ten and fifty degrees. Using these stored curves, the measured sensor capacitance is readily converted, for a given gas temperature, into a dew point measurement of sample gas, and this, in turn may be converted using a table (FIG. 2) to an absolute or relative humidity measurement. Other curves may be used in particular ranges of conditions to simplify measurements, such as capacitance vs. relative humidity, which is largely temperature-independent in a restricted range of conditions. As noted above, however, the response of the sensor to moisture drifts over time, and new calibration curves must be compiled, or the old ones adjusted when the nature of the change can be predicted from a smaller set of calibration points.

The aforementioned drifts due to sensor aging, hysteresis and systematic errors of the measurement instrument may affect the actual sensor response curve by shifting the family of curves shown in FIG. 3 upward or downward. Such a shift may be substantially isometric—that is, may translate the curve without changing its shape or distance between points along the curve. In practical terms such calibration curve drift results in measurement error of about ±1% or more for a commercially available relative humidity sensor. A similar shift occurs in the calibration curves expressed in other common units.

FIG. 3A shows an empirically tabulated set of sensor capacitance vs. temperature curves for different dew points. These curves FIG. 3A may be regarded as a "vertical slice" of the curve family at fixed temperatures shown in FIG. 3.

As can be seen in FIG. 3A, the vertical distance between two points on each curve, represented by sensor capacitance increment $\Delta C$ and taken at two different temperatures (30° C. and 60° C. in FIG. 3A), will remain substantially the same in spite of the upward/downward drift of a curve. At the same time, the increment $\Delta C$ between two fixed temperature points is an increasing function of dew point. More generally, a one-to-one correlation between capacitance increment and dew point of the surrounding gas can be established at any two given temperature points within the range of expected operating conditions.

Applicant uses this correspondence to initially establish the calibration data for a sensor by direct measurement and tabulation of the values $\Delta C$ between two fixed temperatures, and thereafter effects measurements by applying the calibration curves to similarly taken differential measurements. The calibration remains accurate, and is substantially unaffected by "aging" and other sources of error mentioned above. Using this capacitance increment measurement technique a cumulative relative humidity measurement error of less that ±0.02% has been achieved over a one year time without re-calibration Furthermore, these differential measurements may be much more accurate than the single point measurements of the prior art, especially at trace moisture levels. Applicant exploits this property in new measurement protocols, and corresponding apparatus, which are shown and discussed below with reference to FIGS. 4, 4A–4D and 5.

A basic apparatus of the present invention drives the sensor between two temperatures and develops a $\Delta C$ measurement, which is then converted via the stored calibration curves.

Figure 4:
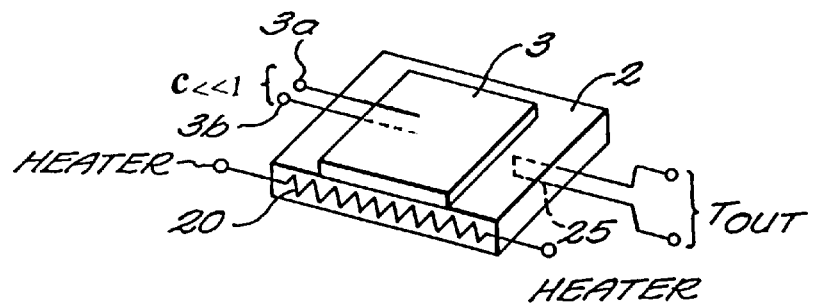
FIGS. 4, 4A, 4B and 4C illustrate sensor embodiments of the invention with heater, cooler or both heater and cooler.

FIG. 4 shows a sensor in accordance with the present invention for improved humidity detection. As shown, the sensor includes a sensing film 3 on a substrate or support 2 wherein electrode contacts 3a, 3b are provided to the upper and lower surfaces of the sensor. A heating element 20 which may for example be formed by a metalized film within the body of or on the surface of support 2 is adapted to provide heat to the assembly for driving the temperature upward, while a thermocouple or other temperature sensing device 25 is formed on or mounted in close proximity to the sensing element 3 to provide a signal which accurately reflects the temperature at the surface. Other forms of heater control are also contemplated. For example, when using a thin platinum film as the heater, temperature control may be achieved by placing the heater in a bridge with two different precision resistors, e.g., via a switch or switch array operating under control of a microprocessor. The resistance values are selected such that their resistance is equivalent or proportional to that of the heater resistance at the specified temperature $T_1$ or $T_2$, and the imbalance voltage developed across the bridge controls the gain of a power supply connected to the heater, so that power is provided to the heater in proportion to its variation from this set resistance value. Thus, the platinum heater is powered until it reaches the desired resistance set point. At this point the computer switches in the other resistor and powers the heater to reach a different temperature. The platinum film lies closely under or may be deposited on one surface of, the sensing film and thus accurately represents the sensing film temperature, although, as noted above, one or more thermocouples may be provided to allow more accurate control, for example to introduce temperature dependent or environment dependent corrections. In a typical system a circuit or microprocessor the takes a sensor reading at each temperature, or at a fixed instant in the temperature cycle, and the successive differences are reported out as the differential or $\Delta C$ sensor value. Thus, the sensor temperature, rather than the ambient temperature, determines the output, and the moisture value is then found by reference to the stored calibration table made for that sensor.

Figure 4A:
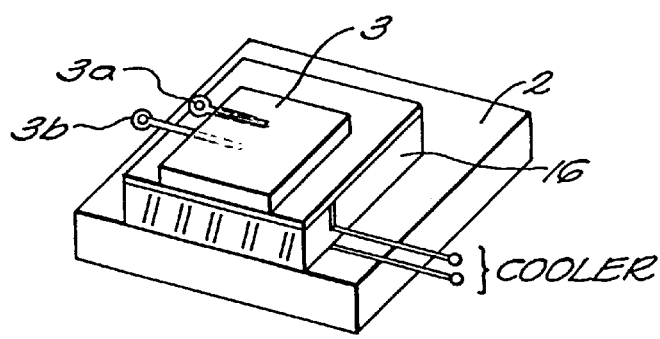

FIG. 4A illustrates another embodiment of a humidity sensor in accordance with the present invention. In this embodiment, a thermoelectric cooler or Peltier effect cooler 16 is provided as the support for the sensing film 3. As before, surface electrodes are provided for detection of changes in the sensor capacitance and a temperature sensor (not shown) may be mounted in an appropriate position to allow determination of the surface temperature. It will be understood that several thermocouples may be provided to allow an automated controller to detect a temperature gradient and extrapolate or interpolate the actual surface temperature, however in general the dimensions are sufficiently small that mounting geometries can provide accurate sensing with a single temperature sensing element. The invention also contemplates embodiments where both a cooler and a heater are provided and each may be energized at different times to separately drive the temperature up or down. It will be understood that each sensor is to be employed in a system wherein an electric circuit or microprocessor controller sets the two different temperatures $T_1$ and $T_2$ to which the relative humidity sensor will be driven and controls another circuit as discussed above, to measure capacitance.

It will further be understood that when a thermoelectric cooler is provided for the sensor, heating may be simply accomplished by reversing the current direction to reverse the heat-cold temperature distribution in the cooler element. Thus, for example, a preset current, for example 200 mA may be continuously supplied to the cooler element and the temperature change may be achieved by reversing the current polarity. At one current direction the sensor is cooled below ambient temperature, while a reversal of current causes the thermoelectric element 16 to work as a heat pump and increase the temperature of the sensor. By monitoring the thermocouple output, the current may be reversed, and sensor capacitance measurements taken at appropriate times. Systems of the present invention may be adapted to to operate with several different temperature differential settings, using a corresponding plurality of calibration curves, to suit different process environments. For instance, referring briefly to FIG. 3A, it will be seen by way of example that for the characteristics of the response curve for minus 40° C. dew point a rather more substantial $\Delta C$ output will be obtained between 20 and 40° C., than will be measured between 40 and 60° C.; accordingly when it is to be used for such low dew point measurements, the system may be calibrated and operated to cycle between these two lower temperatures to enhance the effective sensitivity and range of measurements.

Figure 5:
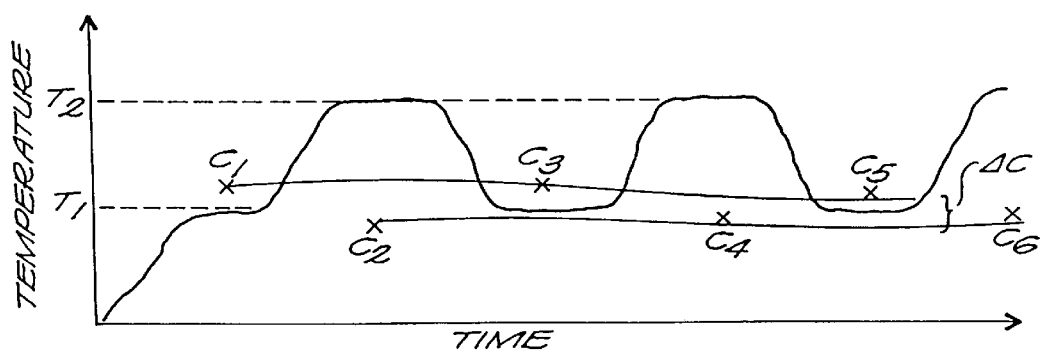
FIG. 5 illustrates system operation according to the method of the present invention.

FIG. 5 shows tone mode of operation of capacitance measurement effected by the present invention. Temperature of the sensor is plotted on the vertical axis against time, and a representative capacitance measurement point indicated in each interval. As the sensor toggles back and forth between temperatures, the sensor capacitance measurement C1, C2, C3 . . . are taken and the processor forms the difference C1–C2, C3–C4, each of which is provided as a $\Delta C$ value. In circumstances where memory effects or fast changes are present in the sensor environment, the controller may use more than one of these values, and may implement signal averaging, smoothing, or other algorithm, such as continuing measurements as these differences converge to a stable value of $\Delta C$. This $\Delta C$ value is then looked up in a previously stored table in which the sensor capacitance difference between these temperatures has been stored for the range of dew points encountered in practice. The processor then outputs the dew point measurement, or the desired equivalent (e.g. relative humidity at ambient) by empirical conversion. It will be understood that a gas temperature or process chamber temperature reading may in general be separately made with high accuracy, and such additional data would then be utilized by the microprocessor for any conversion of dew point to RH or the like.

It has been assumed above that at least two capacitance measurements are performed at two different temperatures but with the same sample gas portion or at least at the same moisture contents. To avoid dynamic error when the moisture concentration is changing in time, moisture sensors with relatively small time response are preferably used, so that the temperature change of the sensor and two consecutive measurements before and after this change thus can be made in a short period of time. One suitable sensor is the commercially available MiniCap2 sensor sold by Panametrics, Inc. of Waltham, Mass. These sensors have a response time less than two seconds in the range of 0 to 180° C., and their small size allows the required temperature change and consecutive capacitance measurements to be made in about a 5 to 20 second time interval using a relatively low power heater, drawing less than one Watt. In most cases this is fast enough for dynamic error to be neglected.

More sophisticated data processing algorithms utilizing more than two data points are also known to those experienced in the field of instrumentation and can be appropriately used with this invention in order to minimize dynamic error. Thus the invention further contemplates systems wherein automated numerical filtering, averaging, fitting, convergence or estimation protocols are applied to the data points, for example with digital measurement signal processing to develop a precise $\Delta C$ measurement, or to correct the measured humidity value in the presence of changing temperature, pressure or humidity conditions.

Furthermore, while the foregoing description relates to a measurement wherein the sensor characteristic is measured at two temperatures and the difference is converted, via stored calibration curve, to a humidity measurement, the salient feature of the invention lies in the accuracy of this measurement, since shifting or drift, whether due to sensor aging, stray capacitance or other common effect, is canceled by the differencing step.

In a further aspect of the invention, the measurement so taken is applied to update or recalibrate a conventional system, such as a single-point sensor system employing, for example, calibration curves such as those of FIG. 3. According to this aspect, a microprocessor controller controls the temperature driver to perform a $\Delta C$ measurement as described above, then compares the humidity value with the values measured at the same time as determined by the stored calibration curves for a single-temperature sensor C output reading. The error function is applied to update the stored curves, which may involve simply shifting the curve up or down, after which the system then continues to operate in a single-temperature reading mode for a period of days, weeks or months. As noted above, the $\Delta C$ correction protocol may be quickly implemented to provide a corrective shift of a single measurement curve in a few seconds. Such a correction protocol obviates the various calibration or correction protocols required in the prior art, such as the periodic provision of calibration sample gases at known relative humidities and laborious recompiling of the calibration table.

Figure 4B:
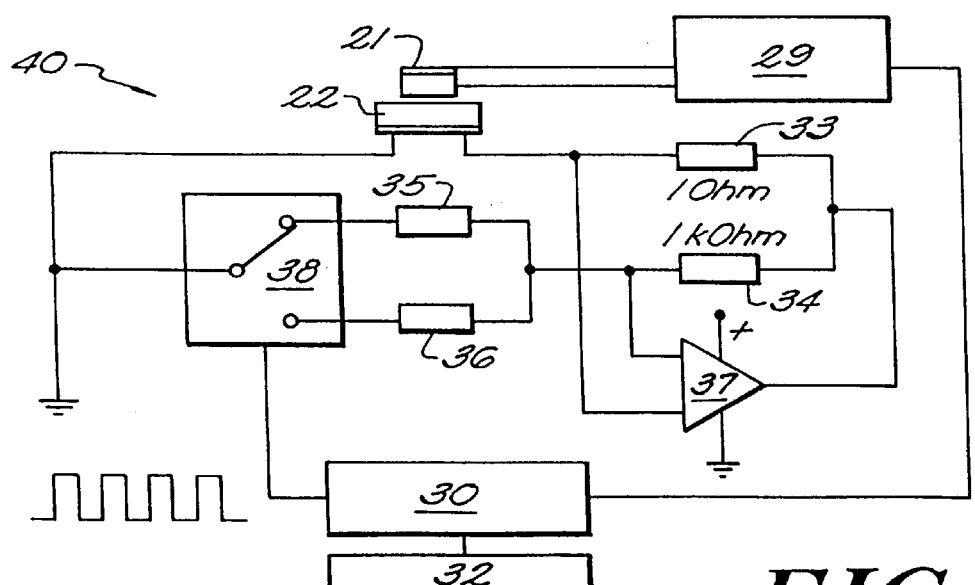
Figure 4C:
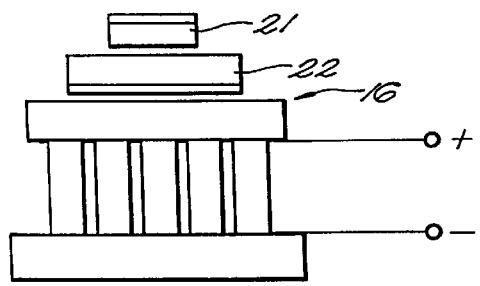
Figure 4D:
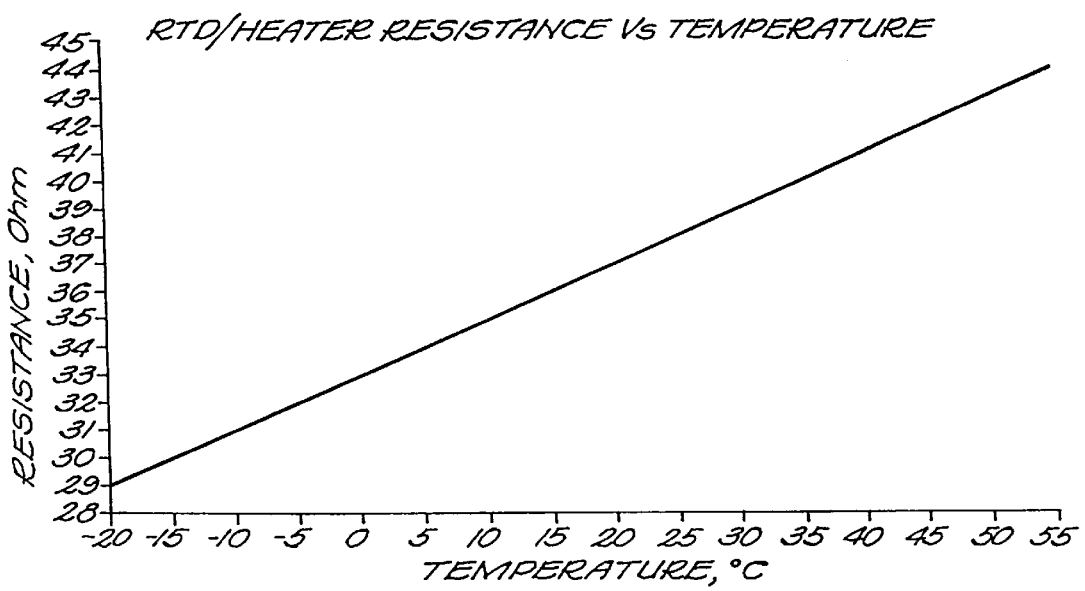
FIG. 4D illustrates heater characteristics of the embodiment of FIG. 4B.

Further details and possible implementations appear in FIGS. 4B–4D. As shown in FIG. 4B, the system may be implemented with a prior art sensing unit, such as a polymer film RH sensing unit 21 on silicon chip having dimensions about 2×2×0.3 mm. This may be a Panametrics' MC-2 polymer RH sensor. The sensor 21 is fixed to a thin film platinum resistive thermal device (RTD) 22 in a manner to secure reliable heat exchange between them. The RTD 22 is used both as a heater and as a temperature sensor for temperature control purposes, thus combining the elements 20,25 of FIG. 4 above. The RTD 22 is connected as shown to the temperature control circuit comprising resistors 33, 34, 35, 36, an amplifier 37 which is powerful enough to supply sufficient power to the bridge, and a solid state switch 38.

The sensor 21 is electrically connected to a digital capacitance measurement bridge or chip 29 which measures the sensor capacitance and/or time variation of capacitance. Both the switch 38 and bridge 29 are connected to a microprocessor-based controller 30. In one embodiment of the invention, the controller 30 implements only one measurement algorithm and uses only one sensor calibration curve, which is initially determined and stored in the memory of the controller 30. In yet another embodiment, the controller 30 is programmed to implement interchangeably two different algorithms using two different calibration curves, as described further below.

When a gas sample with unknown moisture content is applied to the sensor 21, measurement data is collected by controller 30, processed, and displayed on an LCD display 32 in the chosen units of moisture content.

Due to the dynamic nature of the measurement method, fluctuations of sensor output can occur which introduce a dynamic measurement error, especially in cases when the moisture content of the sample gas is changing rapidly or in discrete steps. Applicant has found experimentally that by averaging of several consecutive capacitance increments taken both at temperature increase and decrease, such fluctuation can be reduced or eliminated. For instance, the controller 30 can implement a digital FIR filter to reduce dynamic error. If the calibration curve is reasonably close to linear, then it makes no difference whether the averaging is performed before or after the capacitance reading is converted into a moisture content output determination. Otherwise (for example in the case of capacitance versus Frost Point calibration), it is preferable to average the detected capacitance values first.

The system of FIG. 4B uses the resistance heating element 22 to establish and confirm the preset temperatures at which the sensor reading is taken to establish the thermal capacitance coefficient. A typical plot of the RTD/heater resistance versus its temperature is shown in FIG. 4D. If the maximum ambient temperature is 30° C. the to implement the simple embodiment of FIG. 4B, values of the resistors 35,36 can be chosen close to 40 kΩ and 44 kΩ. In this case the temperature of the RTD 22, and thus of the moisture sensor 21, is conveniently changed between two temperatures close to 35° C. and 55° C., respectively, simply by alternatively connecting either resistor 35 or 36 to the bridge via the switch 38, with controller 30 controlling and monitoring the switching and measurement cycle.

Precision of the resistors 35,36 is not a requirement in practice. The resistors need simply be reasonably stable in time and have a low temperature coefficient.

The moisture content measurement device or system 40 of FIG. 4B may be first calibrated in the following way.

The controller 30 sets temperature cycle of thirty seconds at 55° C. and one minute at 35° C. The sensor capacitance difference at the end of the lower temperature half-cycle and the higher temperature half-cycle is measured. This difference is taken to be the temperature-change-induced sensor capacitance increment or differential measurement ΔC discussed above. A reference gas portion with known moisture content expressed in any chosen units, e.g. Dew/Frost point, is applied to the sensor. When the capacitance increment has become repeatable, it is assumed to be a calibration point of the calibration curve temperature-change-induced capacitance increment versus moisture content. This may take three to five cycles until readings prove to be repeatable. This process is repeated using additional dew point reference gases to obtain the ΔC corresponding to those moisture levels, and complete a calibration table or curve.

To perform measurements of moisture content when then placed in a measurement environment, such as a process gas sampling chamber, the sensor 21 is cycled between the same temperatures and with the same timing as it was done during the calibration process. A gas portion with unknown moisture content is applied to the sensor 21, and the capacitance increment is measured in the same way as just described. The measured ΔC is then converted to a moisture value by reference to the previously obtained calibration curve, and this value is re-calculated in the appropriate moisture units as an output measurement result. The output measurement result is shown on display 32, interfaced to digital control equipment, recorded or otherwise used as final data.

Relatively fast change of moisture content in case of in-situ continuous measurements (e.g., in process control) can result in so-called dynamic error. To reduce dynamic error, the processor may average the four latest capacitance increment values both from temperature decrease and increase steps before determining the moisture value from the stored calibration curve.

Preferably the sensor is operated at low temperature. This results in an increase in Dew/Frost Point sensitivity, because the RH sensitivity is approximately the same over the temperature range of −50° C. to 80° C. Preferably this is done, as described for FIG. 4A, by adding a thermoelectric cooler 16 to the device of FIG. 4B. Such a modified sensor-heater-cooler assembly is shown in FIG. 4C. With such an arrangement, the effective maximum "ambient" temperature on the heater can be dropped from ~30° C. temperature to about −20° C. to −60° C., depending on the cooler type, power and price.

In the case of a relatively inexpensive cooler operable at 30° C. ambient to −20° C., the values of the resistors 35, 36 can be set close to 30 kOhm and 33 kOhm, respectively, which will provide sensor temperature variation between −15° C. and 0° C. A sensitivity of 0.005% RH at −15° C. can then be extended for measurements down to −90° C. Frost Point with ±5° accuracy. When the element 16 can attain a −40° C. lower sensor temperature, the Frost Point measurement sensitivity is sufficient to perform measurements down to −100° C. Frost Point.

In general, both said temperatures can be measured (e.g., in ° C.) in order to be fixed, but absolute temperature values are not, strictly speaking, a necessary requirement. Temperature must be measured only if for any reason it is not possible or expedient to assure that the set temperature at calibration and at measurement are reasonably the same. In this case measured temperature mismatch(es) can be taken into account by standard means commonly employed by engineers for effecting "systematic temperature error compensation."

The above results are striking because it is practically impossible to achieve sensitivity better than about −60° C. with a conventional device based on capacitance versus moisture calibration at constant temperature. This is not only because of the presence of zero drift, but also because the typical requirement of equilibrium between sensor and gas moisture will increase the time required for sensor response to many hours or even days. Applicant's thermal differencing measurement method, on the other hand is free from the latter problem. After the sensor temperature changes, the sensor capacitance will start changing as well in accordance with the extent of water molecule absorption or loss. The speed of absorption and desorption is limited and usually depends on water vapor partial pressure and sensor temperature. As a result, capacitance change more or less lags behind even during the calibration. Thus, at measurement it is not necessary that the data points be sampled when the change is maximum possible, i.e., when equilibrium is reached at each temperature. It just should be measurable with the accuracy dictated by the required moisture measurement accuracy. Thus, at cooler temperatures, timing matters principally because too short temperature variation cycle will reduce sensitivity, while too long a thermal cycle will unreasonably increase sensor time response.

At room temperature (and above) and for RH levels above 5%, timing is usually not a problem, because when either moisture or temperature is changed, near-equilibrium conditions will be reached in seconds. On the other hand, in the range 0.01% RH and $-30°$ C. full equilibrium would only be reached in a matter of days. Thus, at these conditions the temperature cycling period is preferably optimized to achieve a set level of accuracy in an acceptably short time.

A brief discussion of theory follows, from which the advantages of the invention will be more fully appreciated.

There are two known mechanisms of water molecule absorption/desorption. "Weak" physical absorption usually occurs quickly even at low temperatures, with a time constant less than a few minutes. However, chemical desorbtion is slow, occurring on a scale of hours to weeks at the same conditions. It is understood that this division is a rough one, with some phenomena falling in between. Applicant in prototype embodiments of the present invention set the temperature variation cycle between the two time constants for the physical desorption of water molecules and that of chemical desorption. At about a five minute temperature fixed temperature variation cycle, only the quick absorption/desorption mechanism of moisture exchange between sensor surface and gas will be fast enough to follow the temperature change. The slow chemical desorbtion process will result only in what is equivalent to slow zero capacitance change (zero drift), which applicant has shown to not influence accuracy of the measurement. Thus, "true" equilibrium is not required.

By setting the time period for sensitivity to the "quick" desorption only, sensitivity may be reduced as compared with true equilibrium case. However, experiment shows that the ratio between physically absorbed and chemically absorbed molecules remains at least 2:1 even at Frost point down to $-100°$ C. It follows that the use of applicants non-equilibrium sensing method reduces sensitivity by a factor of about 0.7 in the worst case. The exact ratio value will depend on cycle period, individual sensor properties, temperature, etc. It is not necessary to know all these values since in practice with the present invention, the same fixed temperature and cycling period are used at calibration and at measurements as well. Thus the calibration method automatically solves the problem at any Frost Point.

It should also be noted that a small decrease in sensitivity is not important. The long term accuracy is limited not by the capacitance measurement error which can be as low as $\pm 0.001$ pF, but rather by zero drift of the calibration curve. At the same time, the invention provides a sensor speed of response a thousand times better than in case of equilibrium dependent capacitance versus moisture calibration.

From a mathematical point of view, instead of measuring sensor capacitance as a function of moisture content (Function F in equation (2) above) at a constant temperature, applicant measures the first derivative of the same function with respect to temperature. Taking the derivative over temperature T of both left and right sides of the expression (2), one obtains $$\Delta C/\Delta T = \Delta(C_o + \delta C_o)/\Delta T + \Delta F/\Delta T$$

In practice, both temperature measurements are made within no more than a few minutes time interval. $\delta C_o$ is relatively small by itself and is a very slowly changing function of time. It usually takes from about ten seconds to a few minutes to change temperature and perform a capacitance measurement. Because $\delta C_o$ change in a few minutes period is negligible, one obtains $$\Delta(C_o + \delta C_o)/\Delta T \sim \Delta(C_o)/\Delta T.$$

Experimentally, this proves to be a number close to zero (less than 0.02 pF/° C. being typical) and very stable in time, with measured drift as low as less than $\pm 0.0002$ pF/(° C.*year). Moisture content measurement error is therefore less than $\pm 0.002\%$ RH at low RH end.

Now the calibration curve is:

$$\Delta C/\Delta T = (\Delta C_o/\Delta T) + (\Delta F/\Delta T)(\text{moisture}). \tag{3}$$

Taking into account that $\Delta T = (T2-T1) = \text{Const}$, equation (3) can be rewritten:

$$\Delta C = (\Delta F)(\text{moisture}) + \Delta C_o \tag{4}$$

or $$(\Delta F)(\text{moisture}) = \Delta C - \Delta C_o$$

Both $\Delta C/\Delta T$ as the sensor capacitance temperature coefficient and $\Delta C$ as the sensor capacitance increment induced by sensor temperature change are functions of gas moisture content and interchangeably can be used in calibration curves free from $C_o$.

The sensor sensitivity is easily calculated. For a calibration curve in (4), the sensitivity is:

$$\Delta(\Delta F)/[\Delta(\text{moisture})]$$

Temperature cycling period, temperatures, are preferably optimized by well known engineering means to take into account practical factors like random error of capacitance measurements, temperature coefficient, dynamic error minimization, and other considerations. With a sensor system set up at these optimized conditions, e.g. at (T1–T2) $\sim 15°$ C., sensitivity is typically about 80% of the "classical" sensitivity of a conventional system at $-70°$ Frost Point and above, and was found to be between 50% to 70% when operating below $-90°$ C. Frost Point. The RH measurement accuracy at low end (zero drift) was better than $\pm 0.005\%$ RH per year, even when an "average" or typical prior art RH sensor element is used.

This is in contrast to the conventional measurement situation in which sensor capacitance is the sensor output parameter, and which is measured as moisture content representative parameter "on top" of zero capacitance of $C_o$ of $\sim -200$ pF, and with average zero drift $\pm \delta C_0$ of 1% RH or more per year. The method of the present invention measures temperature change induced capacitance increment (or sensor capacitance temperature coefficient as the moisture content representative parameter "on top" of "zero moisture" sensor capacitance increment (or "zero" temperature coefficient) $(\Delta C_o/\Delta T)*(T2-T1)$, a quantity which is usually less than 0.1 pF. By proper sensor selection this value can even be made much less. This new "zero" average drift is less than 0.005% RH per year. Note that below 0.1% RH, the sensor sensitivity is more than 1 pf/% RH. Thus, while the temperature change induced capacitance increment moisture sensitivity is about 50% to 80% of the "classical" capacitance moisture sensitivity, its per year zero drift is more than three hundred times lower. As a result, the measurement accuracy is believed to be at least two hundred times better than the conventional "standard", at least at the low end moisture measurement range.

Calibration curve slope (sensitivity) is known to be much more stable in time than is $C_o$. It may therefore yield better measurement accuracy in practice at around 5% RH. In general, the present invention is considered optimal for 0% to about 5% RH.

Another method contemplated by applicant to solve the dynamic error problem, especially in the range above −70° C., is to use both the present invention and existing measurement system algorithm together. It is a well known correction approach to measure unknown gas concentration of a gas portion with a reliable analyzer, and then apply the same gas to calibrate another analyzer which is installed and measuring the process environment. In this aspect of the present invention, the differential measurement is used first to implement reference moisture measurement instrument and measure the unknown moisture content of a sample gas. Immediately after that, "old" known calibration curve and algorithm are used to make second moisture measurement. This switch in algorithm to implement "old" known moisture measurement device is assumed to be made fast enough so that both measurements are performed with practically the same gas probe. The existing single C calibration curve is then shifted as a whole up or down so that to make the second measurement result agree with, i.e., be numerically the same as, the result obtained by the first (differential) measurement. Thereafter, the shifted calibration curve is used as a single point C reference until the next calibration is made.

It should be noted that in this case part of hardware (sensor, controller, fixtures, etc.) is re-used to interchangeably to carry out the two substantially different measurements with their own different calibration curves and different control/sensing steps. The present invention may also be applied to other sensors which are operated to measure the concentration and/or partial pressure of materials other than water, i.e., any other gas or vapor in a gas mixture sample, since the operation depends simply upon the physics of surface absorption/desorption in a thin film sensor. In that case, an appropriate absorption-type sensor with selectivity to the selected gas or vapor in the gas mixture is employed instead of a moisture sensor.

The invention has been described with reference to specific embodiments and preferred implementations shown in the FIGURES above. However, it will be understood that a great many circuit, control systems and methods and devices for operation and correction of humidity sensors have been developed in the past and are all usable with, and may be incorporated with the improved method and sensors of the present invention. The invention being thus disclosed and described, further variations and modifications will occur to those skilled in the art, and all such modifications and variations are considered to be within the scope of the invention, as set forth in the claims appended hereto.

What is claimed is:

1. A method of measuring moisture content of a gas with an absorption type moisture sensor having a sensor parameter that depends upon moisture content of the gas and that varies with temperature, such method comprising the steps of:
   compiling a calibration curve as a function of an increment of the sensor parameter induced by sensor temperature change between two fixed temperatures and at constant partial pressure of water vapor,
   and measuring an unknown moisture content in a sample gas by
   i) applying the sample gas to said sensor
   ii) changing the temperature of the sensor between two temperatures corresponding at least approximately to said two fixed temperatures, and
   iii) measuring an induced increment of sensor parameter
   wherein the unknown moisture content is determined by looking up the induced increment on the calibration curve to determine a corresponding moisture value.

2. The method of claim 1, wherein the calibration curve is compiled and measurements are performed by cycling the sensor between said two fixed temperatures with a fixed cycling period including a first half cycle for a first temperature and a second half cycle for a second temperature, and said increment is formed from a difference in value of said sensor parameter evaluated, correspondingly, at the end of said first half-cycle and at the end of said second half-cycle.

3. The method of claim 1, comprising the step of controlling temperature of the sensor with an electronic control circuit to determine upper and lower temperatures for defining said induced increment that are substantially the same as the two fixed temperatures of the step of compiling.

4. The method of claim 1, wherein said two fixed temperatures are both kept below ambient sample gas temperature, and above Dew/Frost Point temperature of the sample gas.

5. The method of claim 1, further comprising the step of measuring moisture content by measuring the sensor parameter in the presence of a sample gas and looking up the measured parameter in a calibration table representing sensor parameter as a function of moisture, and wherein the step of measuring an induced increment and looking up the induced increment is performed to recalibrate the table representing sensor parameter as a function of moisture.

6. An apparatus for differential thermal moisture detection to measure moisture in a sample of gas, such apparatus comprising
   a moisture sensor, which outputs an electrical parameter as a definitive function of gas moisture content,
   a temperature changing device thermally connected to the said sensor for changing sensor temperature between two different temperatures, and
   a measurement instrument to measure an increment of said electrical parameter induced by sensor temperature change of the moisture sensor between said two different temperatures, such that variations due to non-equilibrium conditions at the time of measurement cancel out to produce an accurate measurement of moisture in the sample.

7. An apparatus in accordance with claim 6, comprising a controller effective to maintain a temperature cycling period and fixed upper and lower temperatures during performance of a moisture measurement substantially equal to initial values of cycling period and upper and lower temperatures, respectively, set at calibration.

8. An apparatus in accordance with claim 7, wherein said measurement instrument includes means for averaging a number of measurement results measured at each of several consecutive sensor temperature changes.

9. An apparatus in accordance with claim 6, comprising a switch and switch controller operative for connecting a common set of electrical components to interchangeably implement either a differential or a single point sensor measurement.

10. The method of claim 1, wherein the step of measuring an induced increment of said sensor parameter is performed by measuring said parameter at different temperatures and under non-equilibrium conditions.

11. The method of claim 1, wherein the step of measuring an induced increment of said sensor parameter is performed to measure a relative humidity below five per cent.

* * * * *